(12) United States Patent
Young et al.

(10) Patent No.: US 7,722,617 B2
(45) Date of Patent: May 25, 2010

(54) SURGICAL INSTRUMENTATION FOR ROD REDUCTION

(75) Inventors: John Stewart Young, Memphis, TN (US); Douglas D. Kave, Byhalia, MS (US)

(73) Assignee: Warsaw Orthopedic, Inc.

( * ) Notice: Subject to any disclaimer, the term of this patent is extended or adjusted under 35 U.S.C. 154(b) by 1008 days.

(21) Appl. No.: 11/410,742

(22) Filed: Apr. 25, 2006

(65) Prior Publication Data

US 2007/0270869 A1 Nov. 22, 2007

(51) Int. Cl.
A61B 17/88 (2006.01)
(52) U.S. Cl. .................... 606/86 A; 606/99
(58) Field of Classification Search .......... 606/86 A
See application file for complete search history.

(56) References Cited

U.S. PATENT DOCUMENTS

| | | | |
|---|---|---|---|
| 4,856,512 A * | 8/1989 | Lombardo et al. ........... 606/13 |
| 5,020,519 A | 6/1991 | Hayes et al. | |
| 5,160,340 A * | 11/1992 | Gary et al. ................ 606/176 |
| 5,364,397 A | 11/1994 | Hayes et al. | |
| 5,423,855 A | 6/1995 | Marienne | |
| 5,616,143 A | 4/1997 | Schlapfer et al. | |
| 5,720,751 A | 2/1998 | Jackson | |
| 5,910,141 A | 6/1999 | Morrison et al. | |
| 6,036,692 A | 3/2000 | Burel et al. | |
| 6,123,707 A | 9/2000 | Wagner | |
| 6,440,133 B1 | 8/2002 | Beale et al. | |
| 6,648,888 B1 | 11/2003 | Shluzas | |
| 6,660,006 B2 | 12/2003 | Markworth et al. | |
| 6,666,866 B2 | 12/2003 | Martz et al. | |
| 6,790,208 B2 | 9/2004 | Oribe et al. | |
| 6,790,209 B2 | 9/2004 | Beale et al. | |
| 2004/0267275 A1* | 12/2004 | Cournoyer et al. ........... 606/99 |

* cited by examiner

Primary Examiner—Eduardo C Robert
Assistant Examiner—Julianna N Harvey (57) ABSTRACT

One embodiment of the present application includes a surgical instrument comprising a first member and a second member that are pivotally interconnected together. The first member and the second member each include a proximal end structured for manual manipulation by an operator and a distal end defining a gripping nose structured to engage a bone anchor. The instrument further includes a bearing surface to contact an implantable rod when the gripping nose is engaged with a bone anchor and to urge the rod toward the bone anchor when the gripping nose is pivoted thereabout. A thread guide is included that is engaged by threading of a rotatable member. The rotatable member can include a swivel-mounted head structured to bear against and further urge the rod toward a seat in the bone anchor when the rotatable member is turned through the guide.

9 Claims, 7 Drawing Sheets

SURGICAL INSTRUMENTATION FOR ROD REDUCTION

BACKGROUND

The present application relates to a surgical instrument and a manner of using the same, and more particularly, but not exclusively, relates to the reduction of rod components to bone anchors in an orthopedic construct for treatment of a spinal deformity.

The use of surgical instruments to place components in orthopedic constructs has become commonplace. In particular, spinal implant systems frequently include several bone anchors and an interconnecting rod that is shaped to provide a desired spinal curvature. Typically, the bone anchors are implanted first and the rod is then fixed to the bone anchors in succession. As this procedure progresses, some degree of force may need to be applied to reduce the distance between the rod and the next anchor to be connected to it. Accordingly, various instruments have been described to facilitate such rod reduction. In this arena, the desire persists for better rod reducing capability. Thus, there is a need for additional contributions in this area of technology.

SUMMARY

One embodiment of the present application is a unique surgical instrument. Other embodiments include unique methods, systems, devices, instrumentation, kits, and apparatus involving a rod reduction.

A further embodiment of the present application includes a first and second member which are pivotally interconnected and that each include a proximal end opposite a distal end. The proximal ends of the first and second member are structured for manual manipulation by an operator. The distal ends cooperate to form a gripping nose which is structured to engage and rock about a bone anchor. Proximal to the gripping nose is a channel structured to hold a rod while the gripping nose is engaged with the bone anchor. The channel is further structured to urge the rod into a seat in the bone anchor when the gripping nose is rocked about the bone anchor. The instrument also includes a threaded guide and a rotatable member including a threaded portion disposed between its proximal and distal end. This threaded portion engages the threaded guide. With the rotatable member threaded to the guide, the rotatable member can be turned to advance or retract its distal end relative to the seat in the bone anchor while the gripping nose is engaged therewith. In one form, the distal end of the rotatable member further includes a swivel-mounted head.

Another embodiment of the present application includes affixing a bone anchor with a rod receiving portion to a desired spinal location. This embodiment further includes providing a rod structured to extend through the rod receiving portion of the bone anchor and providing a surgical instrument including a rod engagement channel disposed between a first member and a second member that are pivotally interconnected. This surgical instrument further includes a gripping nose to pivotally engage the bone anchor and a rod bearing surface to contact the rod while the gripping nose is engaged with the bone anchor and to urge the rod toward the rod receiving portion of the bone anchor as the gripping nose is moved about the bone anchor. A threaded guide is attached to the instrument, which further includes a rotatable member with a threaded portion structured to engage the threaded guide. When so engaged, the rotatable member can be turned to advance an end of the member to contact the rod positioned in the rod engagement channel. This end can include a swivel-mounted head attached thereto to bear against the rod when the rotatable member is turned.

Yet a further embodiment comprises: affixing a bone anchor including a rod receiving portion and instrumentation engagement structure to a desired spinal location, providing a rod to extend through the rod receiving portion of the bone anchor, positioning the rod between a first member and a second member of an instrument that cooperate to define a rod bearing surface and a gripping nose, pivotally rocking the instrument about the bone anchor while gripping the instrumentation engagement structure with the gripping nose and contacting the rod with the instrument where received in the rod engagement channel to urge the rod into the rod receiving portion of the bone anchor, and turning a rotatable member of the instrument to urge the rod into the rod receiving portion of the bone anchor. This rotatable member is threaded through a guide fixed to one of the first member and the second member.

Still another embodiment of the present application includes a pair of surgical forceps designed to reduce a rod into a bone anchor. The surgical forceps include a gripping nose with means for engaging a bone anchor. A rod engagement channel is also defined by the instrument that includes means for receiving the rod when the gripping nose is engaged with the bone anchor. The rod engagement channel is at least partially defined by a bearing surface to contact the rod and urge it toward a seat in the bone anchor when the gripping nose is moved about the bone anchor. In one form, the instrument further includes a rotatable member, a threaded guide with means for rotatably attaching the rotatable member thereto, and means for advancing the rotatable member towards the bone anchor while the gripping nose is engaged with the bone anchor.

One object of the present application is to provide a unique surgical instrument.

Alternatively or additionally, another object of the present application is to provide a unique surgical method, system, device, instrument, kit and/or apparatus.

Further embodiments, forms, features, aspects, benefits, objects, and advantages of the present application shall become apparent from the detailed description and figures provided herewith.

DETAILED DESCRIPTION OF REPRESENTATIVE EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1:
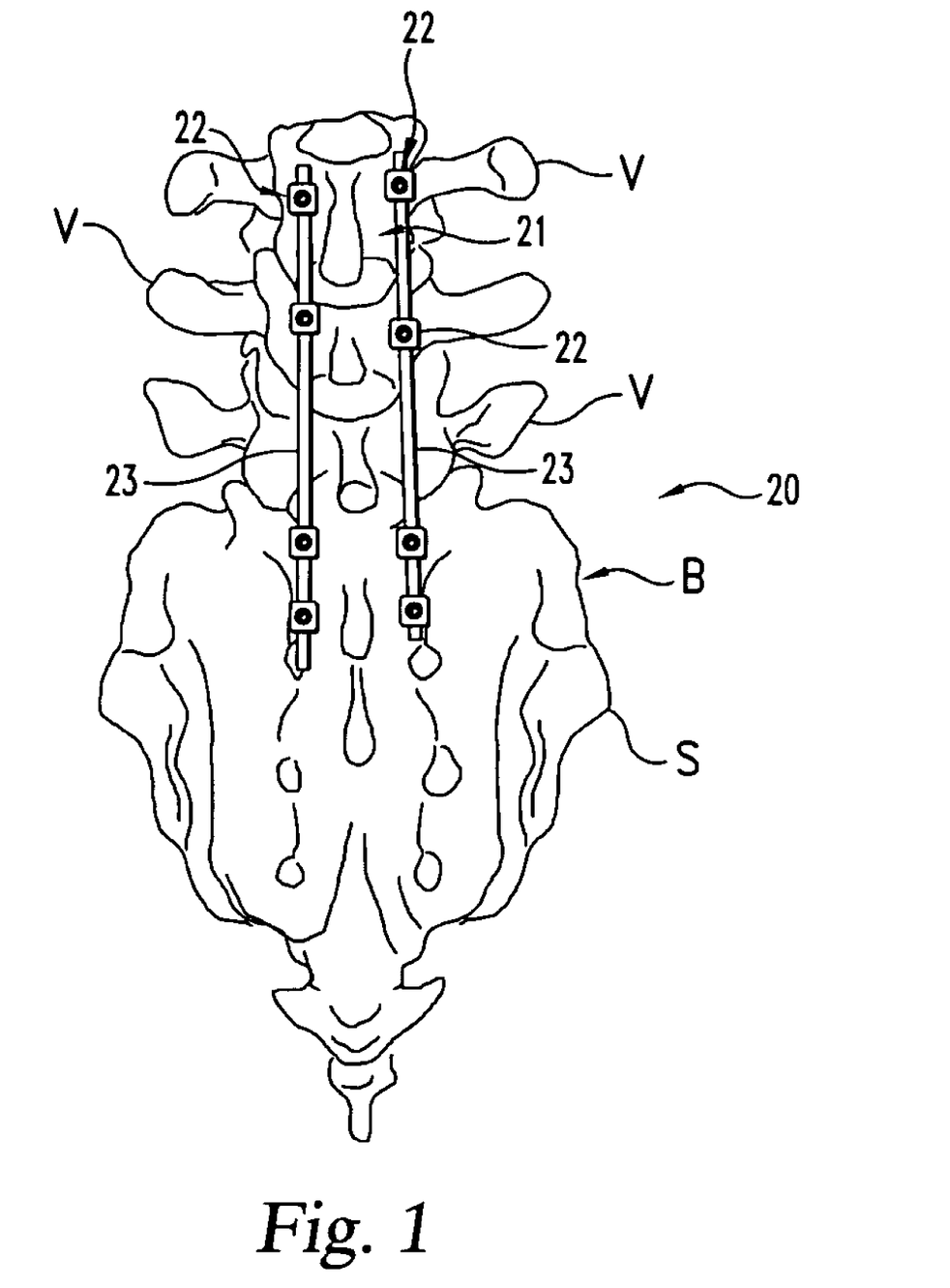
FIG. 1 is a posterior view of a spinal implant system relative to the spinal column of a patient.

FIG. 1 illustrates a posterior spinal implant system 20 as pertains to certain embodiments of the application located at a desired skeletal location of a patient. More specifically, as depicted in FIG. 1, system 20 is affixed to bones B of the spinal column 21 from a posterior approach. Bones B include the sacrum S and several vertebrae V. System 20 generally includes several bone anchors 22 and rods 23 structured to selectively interconnect with bone anchor 22. Rod 23 may be solid or hollow along some or all of its length and/or may be of homogenous or heterogeneous composition. In system 20, bone attachment devices 22 are affixed to various locations of the spinal column 21 and interconnected with rods 23. Posterior fixation system 20 may be used for, but is not limited to, treatment of degenerative spondylolisthesis, fracture, dislocation, scoliosis, kyphosis, spinal tumor, and/or a failed previous fusion.

Figure 2:
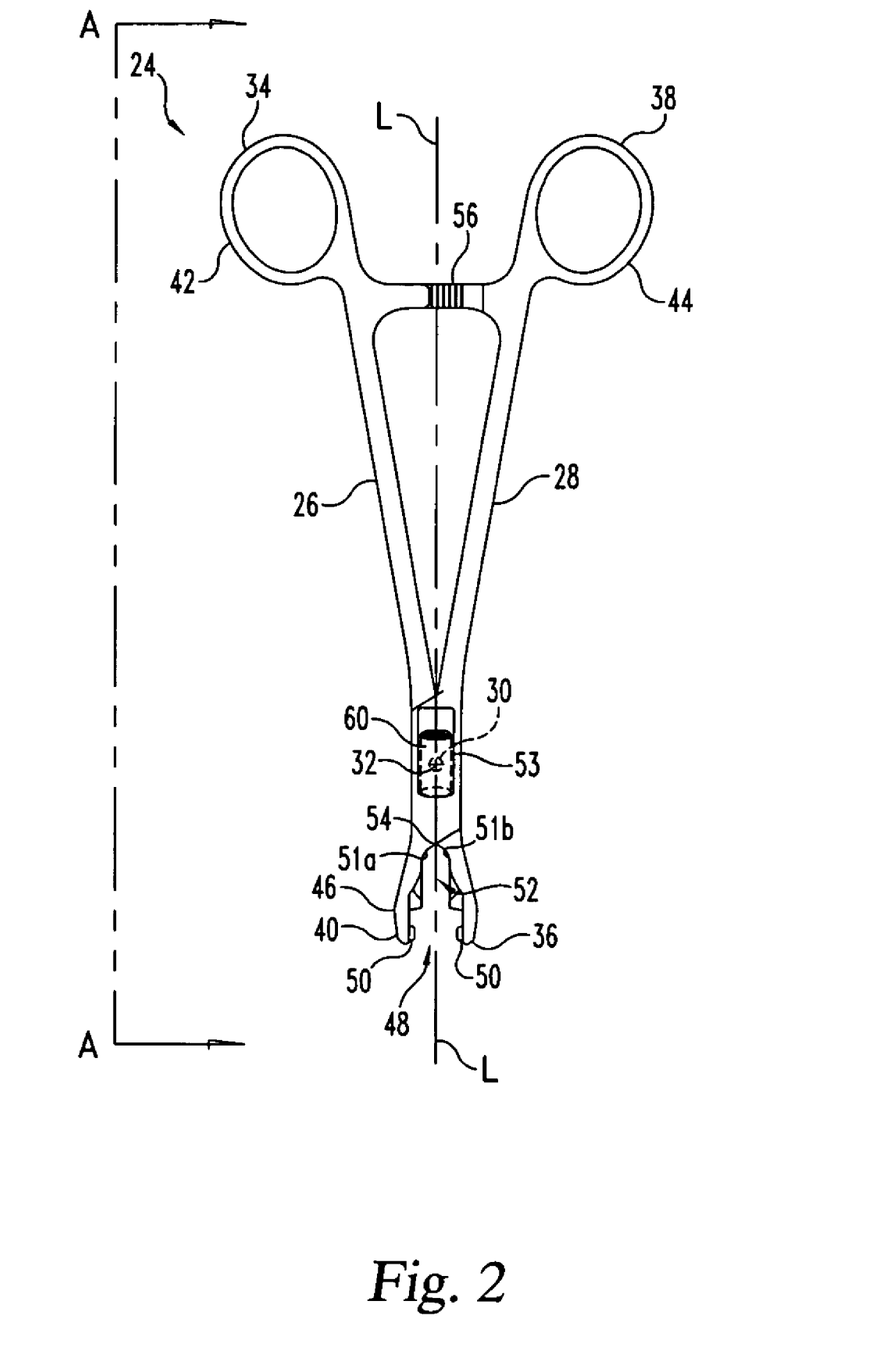
FIG. 2 is a front plan view of a surgical instrument used to reduce a rod in the spinal implant system of FIG. 1, with certain hidden features shown in phantom.

A surgical instrument 24 used to place rod 23 in spinal implant system 20 is shown in a front plan view in FIG. 2, with certain hidden features being shown in phantom. Surgical instrument 24 extends along a longitudinal axis L, including a longitudinal member 26 and a longitudinal member 28 with each having a proximal end portion 34 and 38 opposite a distal end portion 36 and 40, respectively. Member 26 and member 28 are pivotally interconnected via a pivotal coupling 30 to pivot respectively about pivot point 32. Pivot point 32 corresponds to a pivot axis that is perpendicular to the view plane of FIG. 2, and is represented by cross hairs in FIG. 2. Coupling 30 can be provided as a pin that is fixed to one of members 26 or 28 and extends through an aperture in the other of members 26 or 28; a separate pin piece that is secured by swaging, threading, or the like; a hinge; another pivotal coupling of the type used with forceps or scissors, or such different pivotal coupling arrangement as would be known to those skilled in the art.

In the illustrated embodiment of FIG. 2, each of proximal end portions 34, 38 is structured for manual manipulation by a human operator in the form of finger-engageable loop handles 42 and 44. Disposed between handles 42 and 44 is a standard adjustable ratchet mechanism 56 to facilitate fixing instrument 24 in any of a number of different discrete positions. In one form surgical instrument 24 is made of medical grade stainless steel but other embodiments may be composed of, but are not limited to, a different metallic material, and/or a nonmetallic composition.

Figures 4, 5:
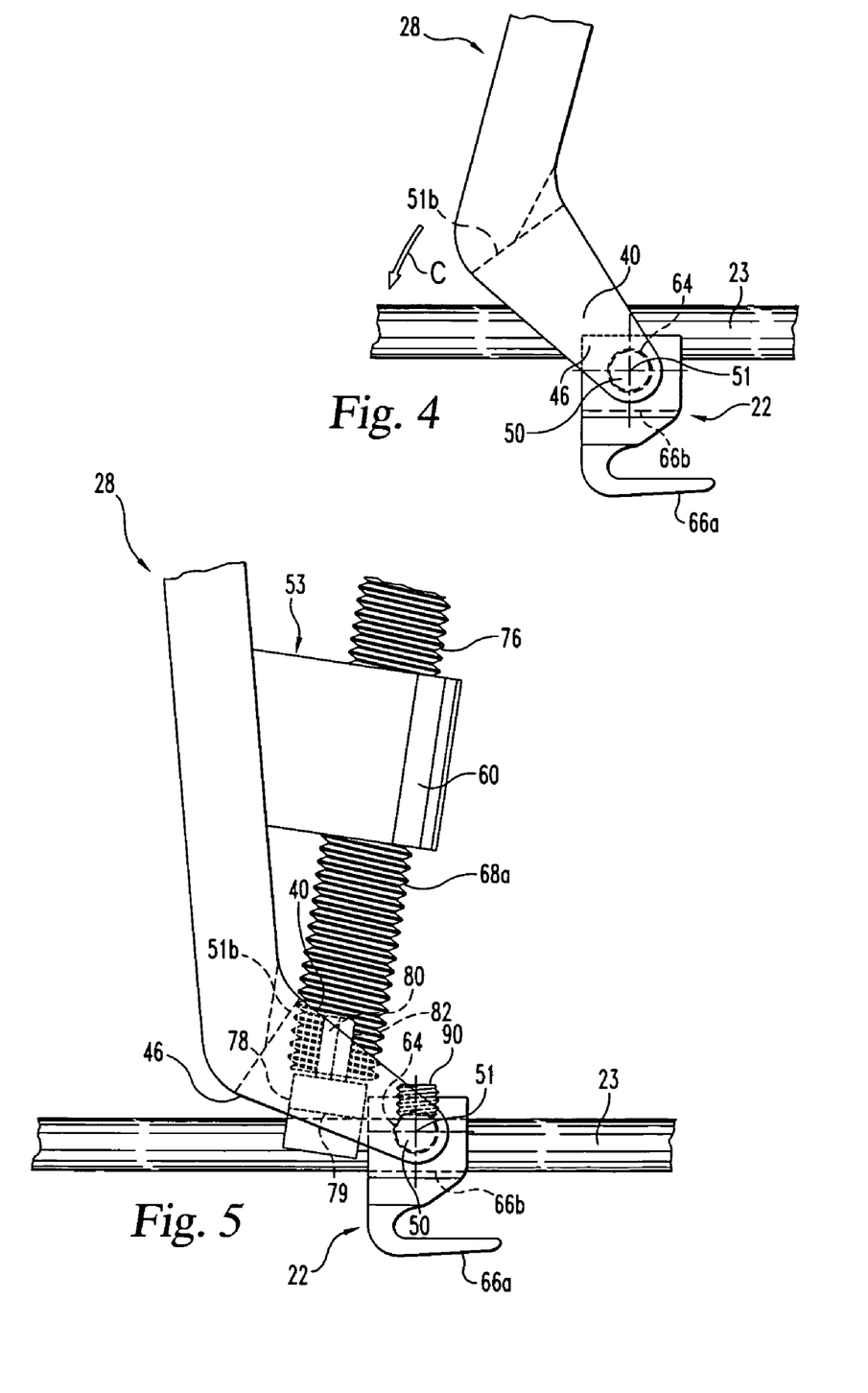
FIG. 4 is a partial side view showing a gripping nose of the surgical instrument shown in FIGS. 2 and 3 while engaged with a bone anchor with a rod positioned above the bone anchor.
FIG. 5 is a partial side view of the surgical instrument in FIGS. 2A and 3A showing the gripping nose engaging a bone anchor and the rotatable member reducing a rod relative to the bone anchor, with certain features being shown in phantom.

Distal end portions 36, 40 are shaped to define a gripping nose 46 which includes a bone anchor engagement portion 48. Bone anchor engagement portion 48 is generally sized and shaped to engage a bone anchor 22 (as shown in FIG. 1). In some embodiments, bone anchor engagement portion 48 includes cylindrical projections 50 sized and shaped to engage corresponding structure in bone anchor 22 as depicted in FIG. 2. For example, projections 50 each engage a corresponding recess 64 in bone anchor 22 as shown in FIGS. 4 and 5 to allow pivotal movement of gripping nose 46 about bone anchor 22. The pivot axis 51 that corresponds to the pivoting/rocking of instrument 24 about bone anchor 22 is represented by cross hairs in FIGS. 4 and 5. Recesses 64 are shown in phantom and are defined in opposing outer side surfaces of bone anchor 22. While projections 50 are shown in cylindrical form, it is contemplated that they could be of a different structure with a complimentary structure provided on bone anchor 22 to provide for suitable engagement therewith. In one form not shown, bone anchor 22 may include projections structured to be received in corresponding slots, grooves, and/or recesses in gripping nose 46 of surgical instrument 24. In alternative embodiments not shown, gripping nose 46 may engage bone anchor 22 by structure(s) including, but not limited to, teeth disposed on the interior of gripping nose 46, or such other means for clamping, hooking, latching, pinning, and/or snapping—to name just a few possibilities.

Figure 2A:
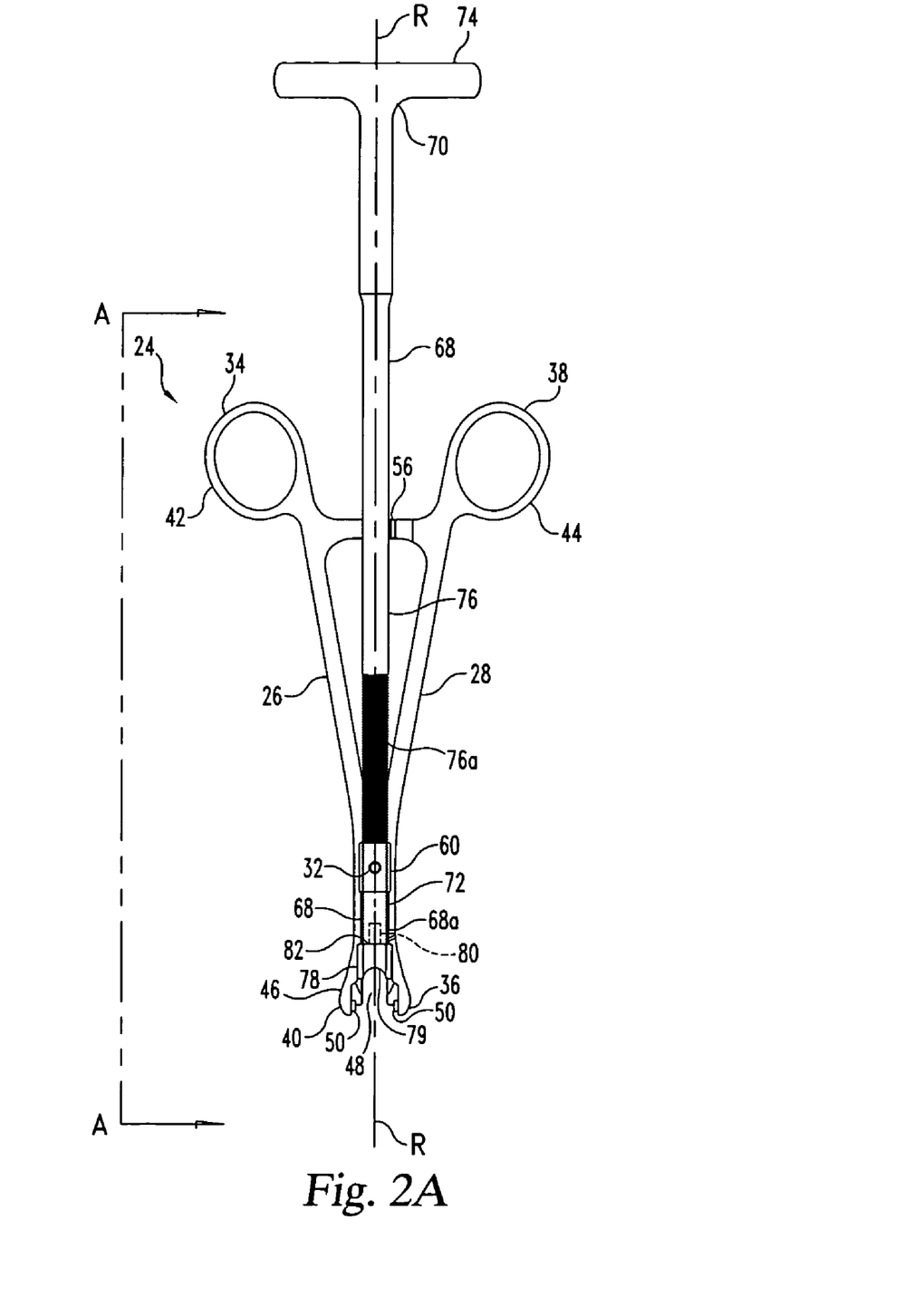
FIG. 2A is a front plan view of the surgical instrument in FIG. 2 further including a rotatable member.
Figure 3:
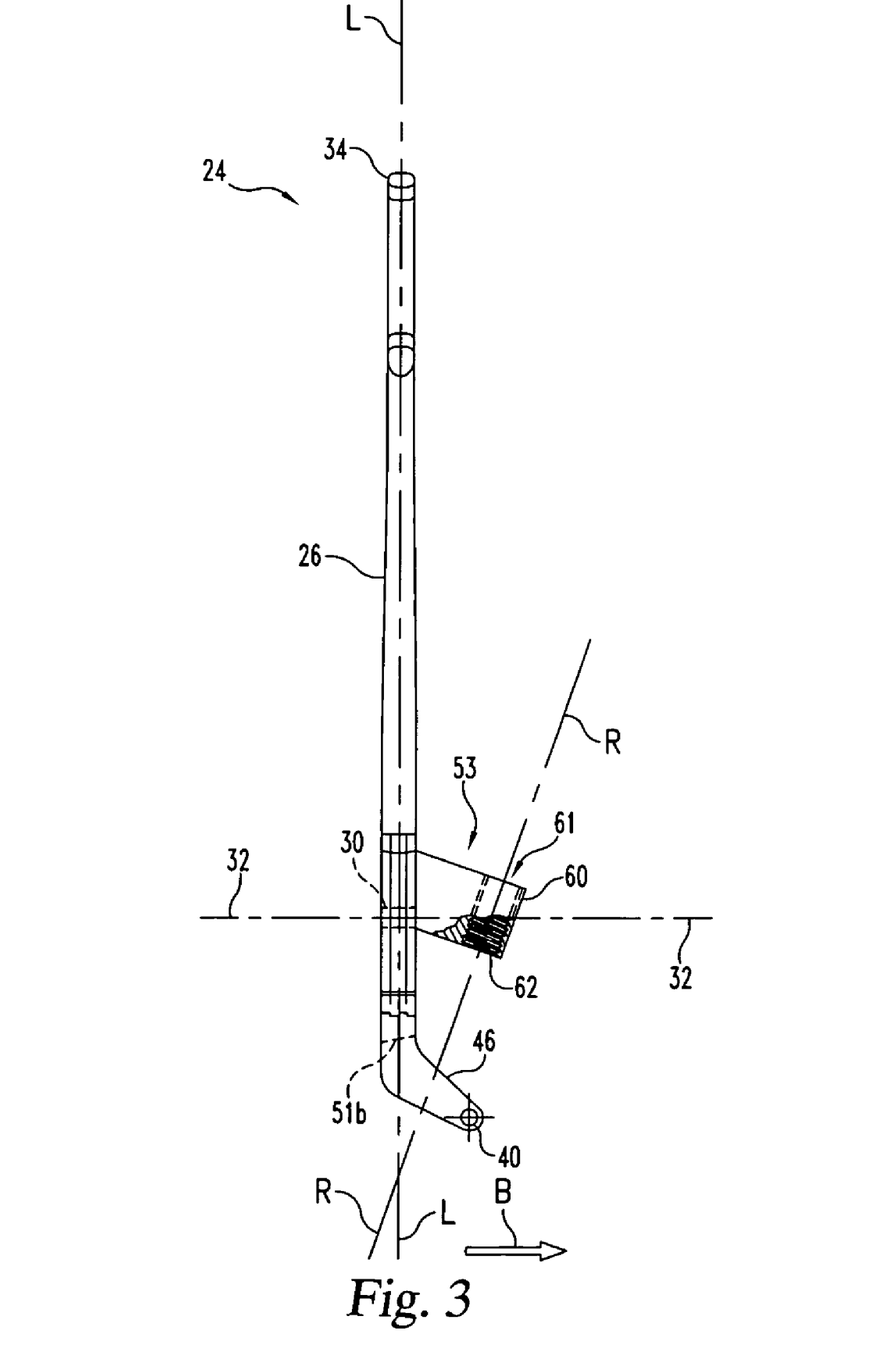
FIG. 3 is a side plan view in partial section of the surgical instrument shown in FIG. 2 that corresponds to view line A-A of FIG. 2.
Figure 3A:
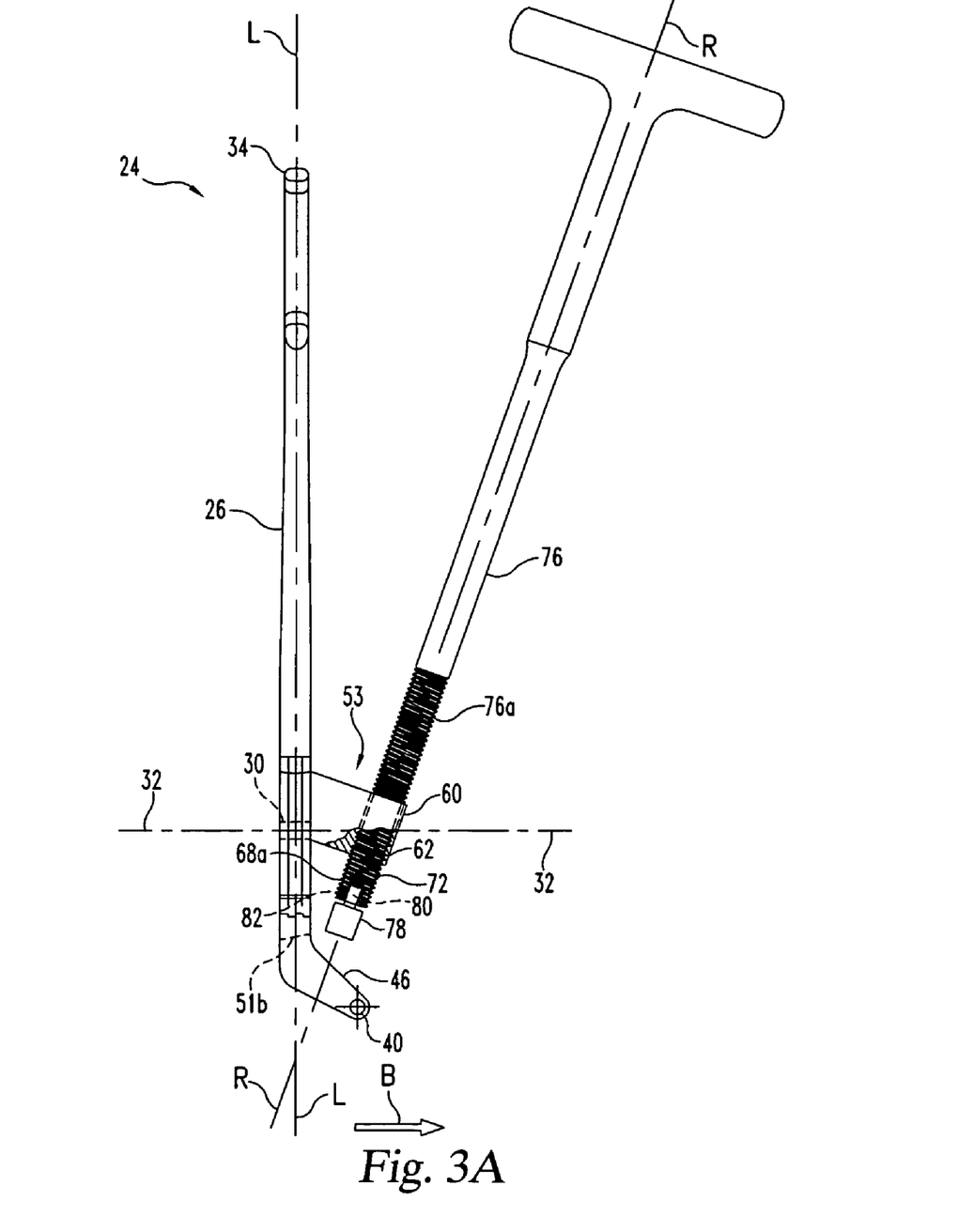
FIG. 3A is a side plan view in partial section of the surgical instrument shown in FIG. 2A that corresponds to view line A-A of FIG. 2A.

Also illustrated in FIG. 2 is a guide 53 for engaging a rotatable member 68 shown in FIG. 2A. As depicted in FIGS. 2 through 3A, sleeve 60 is affixed to member 28 near pivot point 32. In alternative embodiments not shown, sleeve 60 may be attached to member 26. It is contemplated that sleeve 60 may be affixed to surgical instrument 24 via welding, fusing, brazing, chemical bonding, may be integrally forged or machined as a portion of member 26 or 28, and/or provided in a different manner as would occur to those skilled in the art. Sleeve 60 has an aperture 61 therethrough with aperture 61 defining internal threading 62 as shown schematically in FIG. 3.

In alternative embodiments not shown, guide 53 may include clamps for receiving rotatable member 68. The clamps are adjustable and hold a sleeve carried on rotatable member 68 having internal threading so that the threaded portion 76 may be threaded therein and extended to contact rod 23. In an additional alternative embodiment not shown, sleeve 60 includes a gear drive and/or rack and pinion arrangement to engage and selectively move rotatable member 68 relative to sleeve 60 to contact rod 23.

As shown in FIG. 2A, where like numerals refer to like features previously described, surgical instrument 24 is shown assembled with rotatable member 68. Rotatable member 68 includes a proximal end portion 70 and a distal end portion 72. Proximal end portion 70 is structured for manual manipulation by an operator in the form of T-handle 74. In alternative embodiments, proximal end portion 70 may be differently configured. Rotatable member 68 further includes a rod portion 76 with threading 76a structured to engage threading 62 of sleeve 60 such that when rotatable member 68 is turned it moves relative to sleeve 60 about Axis R. Axis R and axis L are coincident in the view plane of FIG. 2A. Distal end portion 72 includes a swivel-mounted head 78 coupled to mounting end portion 68a of rod portion 76. Mounting end portion 68a defines coupling cavity 82. Swivel-mounted head 78 includes a stem 80 which is captured in cavity 82, which is shown in phantom and in which a portion of the threading 76a about rod portion 76 is omitted for clarity in showing cavity 82 and stem 80. When captured in cavity 82 swivel-mounted head 78 rotates about axis R relative to rod portion 76. Swivel-mounted head 78 further includes a rod engagement seat portion 79 structured to engage rod 23. As illustrated, rod engagement seat portion 79 is shaped with a curved surface complimentary to the shape of rod 23. It is contemplated however, that rod engagement portion 79 may vary in configuration.

As illustrated in FIGS. 3 and 3A, where like numerals refer to like features previously described, gripping nose 46 is laterally offset in direction B (as shown by like-labeled arrow) from the longitudinal axis L of instrument 24. In FIG. 3 and FIG. 3A, pivot point 32 is represented by the corresponding pivot axis that is parallel to the view plane. Longitudinal axis L intersects the pivot point 30 and corresponding pivot axis. In alternative embodiments, the offset of gripping nose 46 may extend more or less transversely to the longitudinal axis L. The offset may also be disposed on the opposite side of surgical instrument 24 and laterally extend away in a direction opposite that of direction B. The embodiment of surgical instrument 24 shown in FIG. 3A is the same as that in FIG. 3 except that it further includes rotatable member 68. As shown, threading 76a of rod 76 is engaged with threading 62 of sleeve 60, and swivel-mounted head 78 is assembled to mounting end portion 68a.

As shown in FIG. 2, surgical instrument 24 includes rod bearing surfaces 51a and 51b defined by the distal end portions 36 and 40, respectively. Rod bearing surfaces 51a and 51b define a rod engagement channel 52 proximal to gripping nose 46 and distal to pivotal coupling 30. Rod engagement channel 52 extends toward pivot point 32 along the longitudinal axis L with a proximal end 54 at its most proximal extreme. In alternative embodiments not shown, end 54 may be located more or less closely to pivot point 32. The location of end 54 can be varied in relation to the reduction distance desired. Rod engagement channel 52 is further sized and shaped to secure rod 23 therein when gripping nose 46 is engaged with bone anchor 22, such that projections 50 are positioned in the respective recesses 64 (See FIGS. 4 and 5). As shown, rod engagement channel 52 is structured to engage rod 23 with an approximately cylindrical sectional profile; however, in alternative embodiments, rod engagement channel 52 may be structured to complementarily engage rod 23 with a different profile such as, a square, hexagonal, or octagonal type, to name just a few. When present, rod 23 is tightened in rod engagement channel 52 as member 26 and member 28 are moved toward one another and gripping nose 46 engages bone anchor 22. As illustrated, rod engagement channel 52 is smooth but in alternative embodiments may include additional gripping means such as teeth, knurling, frictional coatings, or the like.

When rod 23 is disposed in rod engagement channel 52 near end 54, rod bearing surfaces 51a and 51b contact rod 23 and urge rod 23 into bone anchor 22 when surgical instrument 24 is pivoted or rocked about bone anchor 22 (and axis 51) as is best seen in FIG. 4, where like numerals refer to like features previously described. FIG. 4 is a partial side view of surgical instrument 24 corresponding to view line A-A of FIG. 2 and FIG. 2A, without rotatable member 68 for clarity purposes. In FIG. 4 bone anchor 22 is illustrated in the form of a bone-engaging hook 66a including a rod seat 66b. In FIG. 4, rod 23 is positioned above rod seat 66b in rod engagement channel 52. The separation distance between rod seat 66b and rod 23 corresponds to the amount of rod reduction desired to position rod 23 in seat 66b. When surgical instrument 24 is pivoted in direction C, as indicated by a like-labeled arrow, rod bearing surfaces 51a and 51b are brought into contact with rod 23. Further movement in direction C forces rod 23 toward bone anchor 22 until rod 23 is received in seat 66b.

FIG. 5 depicts one stage of the reduction procedure associated with rotatable member 68 of surgical instrument 24. In FIG. 5, bone anchor 22 is illustrated in the form of a bone-engaging hook 66a including a rod seat 66b. When gripping nose 46 is engaged with bone anchor 22 and rod 23 situated in rod engagement channel 52 above seat 66b, head 78 of rotatable member 68 may contact rod 23. Once rod engagement portion 79 is seated into contact with rod 23, head 78 becomes rotationally stationary as member 68 is further threaded into guide 60 applying force on rod 23 and urging rod 23 toward seat 66b. In alternate embodiments, head 78 could pivot so that engagement portion 79 could align with and be brought into full surface contact with rod 23.

Once rod 23 is placed in seat 66b as desired, an operator can install a fastener 90 into bone anchor 22 to affix rod 23 thereto. After installation of the fastener 90, ratchet mechanism 56 may be released and first member 26 may be moved away from second member 28 to release surgical instrument 24 from bone anchor 22.

Fastener 90 as illustrated is in the form of a threaded set screw that engages threading of the bone anchor 22. In other embodiments, a different type of fastener may be used. In other alternative embodiments, bone anchor 22 is of a different type such as a bone screw. In one particular bone screw type, multiaxial positioning of a threaded bone-engaging shaft is facilitated by the bone anchor mechanism before fixation with the fastener that holds rod 23 in place.

Figure 6:
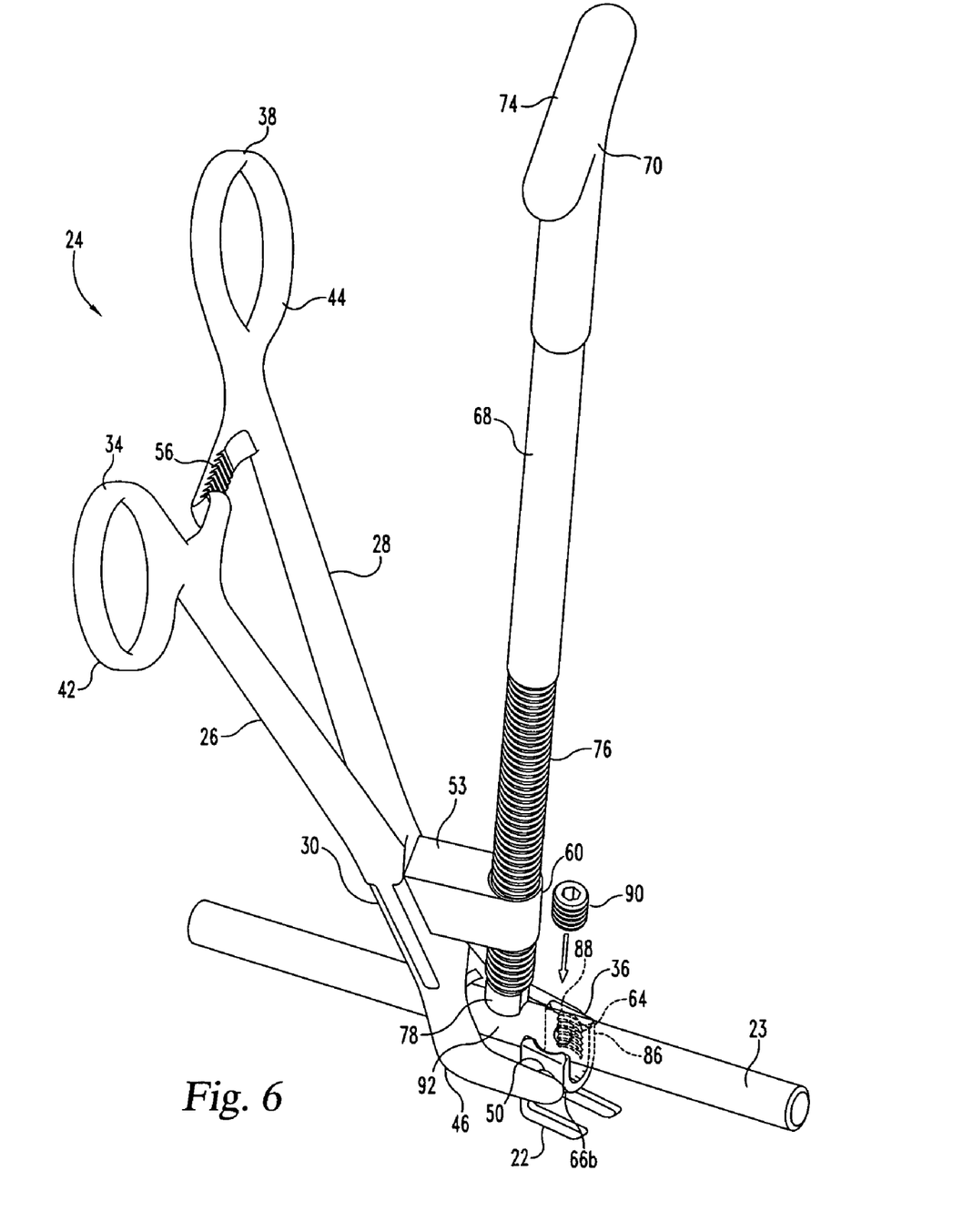
FIG. 6 is a perspective view of the surgical instrument in relation to components of the spinal implant system and illustrates further reducing capabilities thereof.

Referring additionally to the perspective view of FIG. 6, where like reference numerals refer to like features previously described, surgical instrument 24 also includes rotatable member 68 where threading 76a of rod portion 76 is engaged with sleeve 60 of guide 53. As shown, sleeve 60 is further structured and affixed to surgical instrument 24 such that when extended through sleeve 60, rotatable member 68 contacts rod 23 at interface 92 between portions 36 and 40 and between channel 52 and anchor engagement portion 48.

As illustrated in FIG. 6 gripping nose 46 of surgical instrument 24 is engaged with bone anchor 22. Bone anchor 22 includes a rod receiving portion 84 formed by pair of upright channels 86 and includes seat 66b. Cylindrical projections 50 are engaged with recesses 64 to allow pivotal movement of surgical instrument 24 about bone anchor 22. Rod 23 is also secured in rod engagement channel 52 above rod receiving portion 84.

In one form, rotatable member 68 may be turned in a direction to move swivel-mounted head 78 into contact with rod 23 at interface 92. As rotatable member 68 is further turned, rod 23 is urged between upright channels 86 into rod receiving portion 84 until it is placed in seat 66b. Once rod 23 is in place, fastener 90 may be engaged with channel threading 88 to secure rod 23 thereto and create a rigid construct. Once the fastener 90 is inserted, rotatable member 68 may be turned in the opposite rotational direction to retract it away from rod 23 and surgical instrument 24 may be disengaged from bone anchor 22.

In an alternative embodiment, once rod 23 is seated in bone anchor 22 rotatable member 68 may be moved away from rod 23. Surgical instrument 24 may then be further pivoted about bone anchor 22 to change interface 92 and then rotatable member 68 may be turned until rod 23 contacts seat 66b of bone anchor 22. Once rod 23 is securely held in rod receiving portion 84 fastener 90 may be inserted and surgical instrument 24 may be removed from bone anchor 22.

While not shown in FIG. 6 it should be understood that rod 23 may also be reduced to bone anchor 22 by pivoting gripping nose 46 about bone anchor 22 to bring rod bearing surfaces 51a and/or 51b into contact with rod 23 to urge rod 23 into rod receiving portion 84 as described in relation to FIG. 4. This reduction action may be made done individually or in combination with the reduction action achieved through use of rotatable member 68.

While the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected. Any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present invention and is not intended to limit the present invention in any way to such theory, mechanism of operation, proof, or finding. In reading the claims, words such as "a", "an", "at least on", and "at least a portion" are not intended to limit the claims to only one item unless specifically stated to the contrary. Further, when the language "at least a portion" and/or "a portion" is used, the claims may include a portion and/or the entire item unless specifically stated to the contrary.

What is claimed is:

1. A surgical instrument to place a rod into a bone anchor of a spinal implant system, comprising:
    a first member and a second member pivotally interconnected by a pivot coupling, the first member including a first proximal end portion opposite a first distal end portion and the second member including a second proximal end portion opposite a second distal end portion, the first proximal end portion and the second proximal end portion being structured for manual manipulation of the instrument by an operator, and the first distal end portion and the second distal end portion defining a gripping nose including a bone anchor engagement portion shaped and sized to engage the bone anchor, and
    a rod engagement channel sized and shaped to receive the rod when the gripping nose engages the bone anchor, the rod engagement channel being positioned proximal to the gripping nose, the gripping nose being structured to rock about the bone anchor when engaged with the bone anchor to urge the rod positioned in the rod engagement channel towards a seat in the bone anchor;
    a guide fixed to one of the first member and the second member, the guide including threading; and
    a rotatable member including a proximal portion opposite a distal portion, the rotatable member including a threaded portion between the proximal portion and the distal portion, the rotatable member being structured to rotatably engage the threading of the guide with the threaded portion, the distal portion including a swivel-mounted head to bear against the rod and urge the rod towards the seat of the bone anchor by turning the rotatable member relative to the guide to move the swivel-mounted head towards the bone anchor when the gripping nose is engaged thereto.

2. The surgical instrument of claim 1 wherein the instrument has a longitudinal axis intersecting a pivot point defined by the pivot coupling, the gripping nose has a longitude extending in a direction laterally offset from the longitudinal axis, the rod engagement channel is elongated along the longitudinal axis, and the distal portion of the rotatable member threadingly engaged with the guide is structured to bear against the rod positioned in the rod engagement channel at a location between the rod engagement channel and the bone anchor engagement portion of the gripping nose.

3. The surgical instrument of claim 1 wherein the bone anchor engagement portion of the gripping nose includes a first projection extending from the first distal end portion and a second projection extending from the second distal end portion, the first projection is structured to pivotally engage a corresponding first bone anchor recess, and the second projection is structured to pivotally engage a corresponding second bone anchor recess.

4. The surgical instrument of claim 1 wherein:
    the instrument has a longitudinal axis intersecting a pivot point defined by the pivot coupling and the first proximal end portion and the second proximal end portion line along the longitudinal axis:
    the gripping nose has a longitude extending in a direction laterally offset from the longitudinal axis;
    the guide is fixed to the one of the first member and the second member at the pivot coupling and extends from the one of the first member and the second member in a direction laterally offset from the longitudinal axis.

5. The surgical instrument of claim 1 wherein the guide is in the form of a sleeve structured to circumscribe the rotatable member, and the threading is internal to the sleeve.

6. The surgical instrument of claim 1 wherein the first proximal end portion and the second proximal end portion define a ratchet and one or more finger engageable handles.

7. The surgical instrument of claim 1 wherein the proximal portion of the rotatable member includes a handle structured to manually turn the rotatable member.

8. The surgical instrument of claim 1, wherein the distal end portions of the first and second members each include a distal end surface defining a rod bearing surface portion of the rod engagement channel at a location that is proximal to the gripping nose and distal to the pivot coupling of the first and second members.

9. The surgical instrument of claim 8, wherein the rod engagement channel extends along the longitudinal axis from a proximal end located adjacent the pivot coupling to an opposite distal end.

* * * * *